United States Patent
Irisawa et al.

(10) Patent No.: US 10,709,336 B2
(45) Date of Patent: *Jul. 14, 2020

(54) PHOTOACOUSTIC IMAGE GENERATION APPARATUS AND METHOD

(71) Applicant: FUJIFILM Corporation, Tokyo (JP)

(72) Inventors: Kaku Irisawa, Ashigarakami-gun (JP); Kazuhiro Hirota, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 317 days.

This patent is subject to a terminal disclaimer.

(21) Appl. No.: 15/457,742

(22) Filed: Mar. 13, 2017

(65) Prior Publication Data

US 2017/0181639 A1   Jun. 29, 2017

Related U.S. Application Data

(63) Continuation of application No. 14/622,084, filed on Feb. 13, 2015, now Pat. No. 9,629,557, which is a continuation of application No. PCT/JP2013/004864, filed on Aug. 15, 2013.

(Continued)

(30) Foreign Application Priority Data

Aug. 17, 2012 (JP) ................... 2012-180723
Aug. 13, 2013 (JP) ................... 2013-168095

(51) Int. Cl.
*A61B 5/00* (2006.01)

(52) U.S. Cl.
CPC .......... *A61B 5/0095* (2013.01); *A61B 5/7225* (2013.01); *A61B 5/7257* (2013.01); *A61B 5/742* (2013.01); *A61B 2576/00* (2013.01)

(58) Field of Classification Search
CPC ..... A61B 5/0095; A61B 5/722; A61B 5/7252; A61B 5/742
See application file for complete search history.

(56) References Cited

U.S. PATENT DOCUMENTS 4,541,281 A   9/1985   Chubachi et al.
4,594,662 A *  6/1986   Devaney ............. G01S 15/8977
                                                  128/916

(Continued)

FOREIGN PATENT DOCUMENTS

JP   05-237094 A    9/1993
JP   2009-537201 A  10/2009

(Continued)

OTHER PUBLICATIONS

Hu, "Photoacoustic imaging and characterization of the microvasculature", Journal of Biomedical Optics 15(1), 011101, Jan./Feb. 2010 (Year: 2010).*

(Continued)

*Primary Examiner* — Joanne M Hoffman
(74) *Attorney, Agent, or Firm* — Birch, Stewart, Kolasch & Birch, LLP

(57) ABSTRACT

After light has been output to a subject to be examined, a photoacoustic wave induced in the subject by the output light is detected. It is assumed that at least one virtual detector element is present outside of a real detector, and dummy data corresponding to the at least one virtual detector element are added to photoacoustic data in which pieces of data of the photoacoustic wave detected by the detector are arranged in accordance with the positions of detector elements. A photoacoustic image is generated by reconstructing the photoacoustic data to which the dummy data have been added by using a Fourier transform method.

22 Claims, 12 Drawing Sheets

(56) References Cited

U.S. PATENT DOCUMENTS

| | | | | |
|---|---|---|---|---|
| 5,610,967 | A | * | 3/1997 | Moorman .............. A61B 6/06 378/141 |
| 6,216,540 | B1 | | 4/2001 | Nelson et al. |
| 2009/0297008 | A1 | | 12/2009 | Taxt et al. |
| 2012/0050710 | A1 | | 3/2012 | Oishi |
| 2012/0281902 | A1 | | 11/2012 | Oikawa et al. |
| 2013/0114859 | A1 | * | 5/2013 | Wanda .............. A61B 5/0095 382/103 |
| 2013/0139567 | A1 | | 6/2013 | Madsen et al. |

FOREIGN PATENT DOCUMENTS

| | | |
|---|---|---|
| JP | 2010-011904 A | 1/2010 |
| JP | 2010-035806 A | 2/2010 |
| JP | 2012-139475 A | 7/2012 |

OTHER PUBLICATIONS

Wang, "An Imaging Model Incorporating Ultrasonic Transducer Properties for Three-Dimensional Optoacoustic Tomography", IEEE Transactions on Medical Imaging, vol. 30, No. 2, Feb. 2011 (Year: 2011).*

Rourmeliotis, "Real-time Three-dimensional Photoacoustic Imaging", The University of Western Ontario, Aug. 2011 (Year: 2011).*

Changhui li, "High-numerical-aperture-based virtual point detectors for photoacoustic tomography" Appl Phys Lett, 93(3) (Year: 2008).*

Yang, "Photoacoustic tomography of a rat cerebral cortex with a ring-based ultrasonic virtual point detector", J. of Biomedical Optics, 12(6) (Year: 2007).*

Yang, "Ring-based ultrasonic virtual point detector with applications to photoacoustic tomography" Appl. Phys. Lett. 90 (Year: 2007).*

International Search Report issued in PCT/JP2013/004864 dated Oct. 8, 2013.

Written Opinion of the International Searching Authority issued in PCT/JP2013/004864 dated Oct. 8, 2013.

Advanced Engineering Mathematics, 2nd Ed., Michael D. Greenbert, 1998, page: back inside covers.

Math Warehouse, trigonometry, Jul. 2012, http://www.mathwarehouse.com/trigonometry/sine-cosine-tangent-practice3.php.

School for Champions, Doppler Effect Equation, 2010, http://www.school-for-champions.com/science/sound_doppler_effect_equations.htm.

* cited by examiner

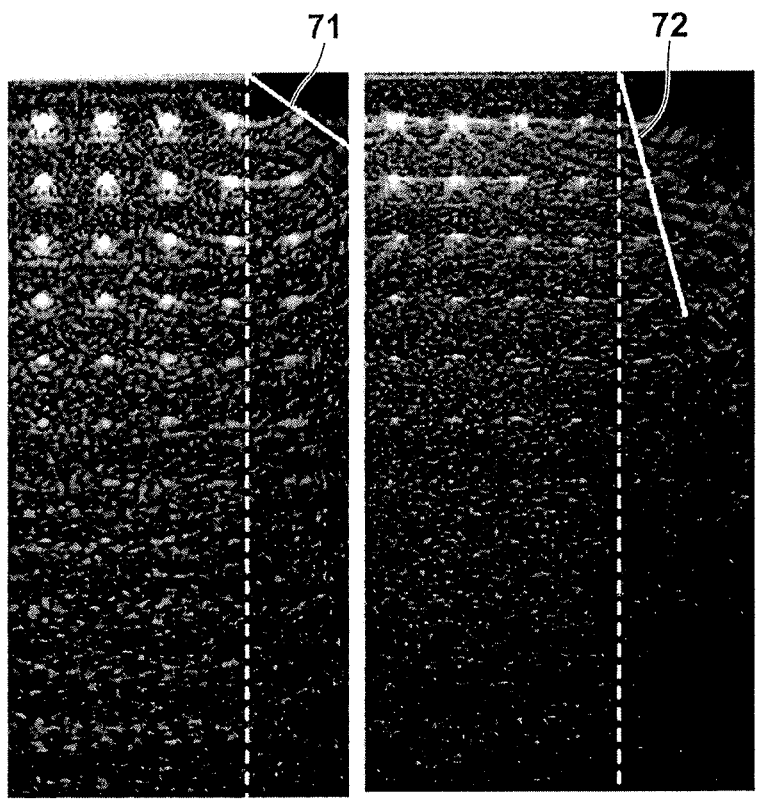
FIG.7A  FIG.7B
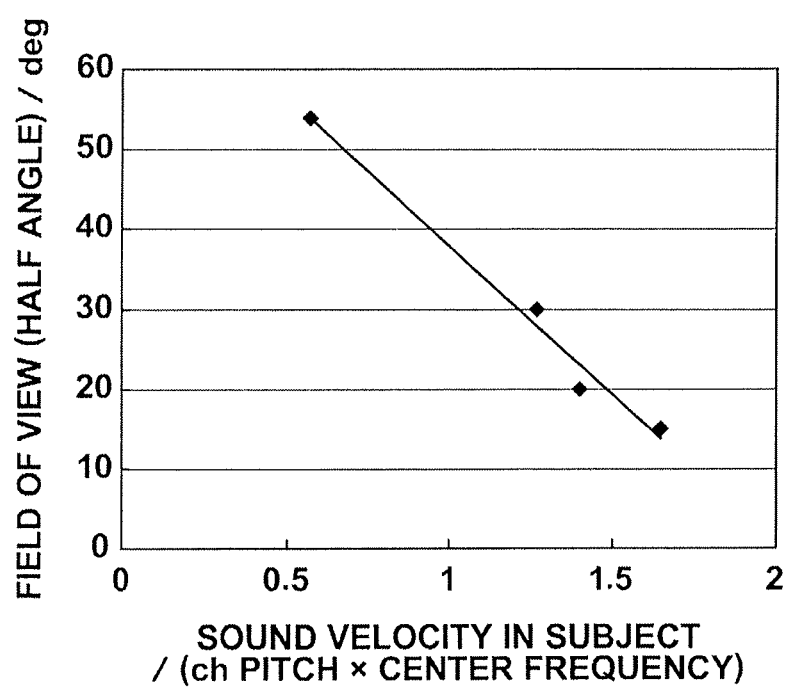
FIG.8

PHOTOACOUSTIC IMAGE GENERATION APPARATUS AND METHOD

SUMMARY OF THE INVENTION

Ultrasonic imaging and photoacoustic imaging differ from each other in that a reflection ultrasound induced at a position to which an ultrasound has been sent is detected in ultrasonic imaging while a photoacoustic wave induced at a position that has been illuminated with light is detected in photoacoustic imaging. In photoacoustic imaging, light is output not only to a region of a subject to be examined corresponding to an area in which detector elements of an ultrasonic detector are present, in other words, a region of a subject to be examined to which an area in which the detector elements are present is projected, perpendicularly to an ultrasound detection surface, in the depth direction of the subject to be examined. The light is often output also to a region of the subject to be examined outside of the region corresponding to the area in which the detector elements are present. In that case, a photoacoustic wave from the region outside of the region corresponding to the device area of the photoacoustic wave detector is detected, especially, at end parts of the device area. When photoacoustic signals including a detection signal of such a photoacoustic wave are reconstructed by using a Fourier transform method, light absorbing material outside of the device area is folded over into the device area, and that has caused an artifact in some cases. In Patent Document 1, the photoacoustic image generated by the Fourier transform method is combined with a photoacoustic image generated by the time domain method. Consequently, it is possible to reduce an influence of the artifact present in the photoacoustic image generated by the Fourier transform method. However, it is impossible to suppress the artifact, itself, present in the photoacoustic image generated by using the Fourier transform method.

In view of the foregoing circumstances, it is an object of the present invention to provide a photoacoustic image generation apparatus and method that can suppress artifacts caused by a photoacoustic wave from a region outside of a region that corresponds to a device area when a photoacoustic image is generated by using the Fourier transform method.

To achieve the aforementioned object, the present invention provides a photoacoustic image generation apparatus including an acoustic wave detection means that includes a plurality of detector elements that are at least linearly arranged, and detects, after light has been output to a subject to be examined, a photoacoustic wave induced in the subject by the output light, a dummy data addition means that assumes that at least one virtual detector element is present outside of the plurality of detector elements that are at least linearly arranged, and adds dummy data corresponding to the at least one virtual detector element to photoacoustic data in which pieces of data of the photoacoustic wave detected by the plurality of detector elements in the acoustic wave detection means, respectively, are arranged in accordance with the positions of the detector elements, and an image generation means that generates a photoacoustic image by reconstructing the photoacoustic data to which the dummy data have been added by using a Fourier transform method.

In the present invention, the number of the at least one virtual detector element may be determined based on the element size of the detector element in a direction of arrangement of the detector elements in the acoustic wave detection means and a center frequency of the detector elements.

The number of the at least one virtual detector element may be determined based on a length represented by $D(f) \times \tan \alpha$, where an angle from a straight line perpendicular to an acoustic wave detection surface in the acoustic wave detection means, and the angle being determined based on a product of the element size and the center frequency, is $\alpha$, and the center frequency is f, and a depth determined based on the center frequency f is $D(f)$.

The angle $\alpha$ may be determined based on a value obtained by dividing the sound velocity of an acoustic wave traveling in the subject to be examined by the product of the element size and the center frequency.

The depth $D(f)$ may represent a maximum depth at which a signal to noise ratio higher than a predetermined value is obtained when the detector elements having the center frequency f are used.

The number of the at least one virtual detector element may be determined based on a value obtained by dividing the length represented by the product of $D(f)$ and $\tan \alpha$ by a channel pitch of the (virtual) detector elements.

The apparatus may further include an image mask means that masks, in the generated photoacoustic image, an area outside of a straight line extending, at the angle $\alpha$, from a pixel corresponding to a detector element at an end of the plurality of detector elements, which are at least linearly arranged, toward an area in which the dummy data have been added.

The dummy data addition means may assume that the at least one virtual detector element is present on both sides of the linearly arranged plurality of detector elements in a direction of arrangement of the detector elements, and add the dummy data.

The number of the at least one virtual detector element may be determined in advance for each acoustic detection means to be used.

The dummy data may be 0 (the value of zero).

The reconstruction by using the Fourier transform method includes, for example, two-dimensional Fourier transform on the photoacoustic data to which the dummy data have been added. In the reconstruction by using the Fourier transform method, the reconstruction may be performed after components higher than or equal to a predetermined frequency in a direction of arrangement of the detector elements are cut in the photoacoustic data on which the two-dimensional Fourier transform has been performed.

The reconstruction by using the Fourier transform method may include two-dimensional inverse Fourier transform on the photoacoustic data on which the two-dimensional Fourier transform has been performed. The two-dimensional inverse Fourier transform may be performed by performing inverse Fourier transform in the direction of arrangement of the detector elements after performing inverse Fourier transform in a direction orthogonal to the direction of arrangement of the detector elements.

Further, the present invention provides a photoacoustic image generation method including the step of detecting, after light has been output to a subject to be examined, a photoacoustic wave induced in the subject by the output light by using an acoustic wave detection means including a plurality of detector elements that are at least linearly arranged, the step of assuming that at least one virtual detector element is present outside of the plurality of detector elements that are at least linearly arranged, and adding dummy data corresponding to the at least one virtual detector element to photoacoustic data in which pieces of data of the photoacoustic wave detected by the plurality of detector elements in the acoustic wave detection means, respectively, are arranged in accordance with the positions of the detector elements, and the step of generating a photoacoustic image by reconstructing the photoacoustic data to which the dummy data have been added by using a Fourier transform method.

The photoacoustic image generation apparatus and method of the present invention assumes that at least one virtual detector element is present outside of a plurality of detector elements that are at least linearly arranged, and adds dummy data corresponding to the at least one virtual detector element to real data of photoacoustic waves detected by detector elements in the photoacoustic detection means. Further, a photoacoustic image is generated from the photoacoustic data to which the dummy data have been added by using a Fourier transform method. Therefore, it is possible to reduce a wrap-around noise, which is produced when reconstruction by the Fourier transform method is performed without adding dummy data, and to obtain a photoacoustic image in which artifacts are suppressed. Further, it is possible to increase the width of the photoacoustic image in a lateral direction (a direction of arrangement of the detector elements) by a width corresponding the added dummy data. Therefore, it is possible to generate an image representing a wider range of the subject to be examined.

BRIEF DESCRIPTION OF THE DRAWINGS

FIG. 7A is a diagram illustrating a photoacoustic image obtained by reconstructing data including dummy data;

FIG. 7B is a diagram illustrating a photoacoustic image obtained by reconstructing data including dummy data;

FIG. 8 is a graph showing a relationship between marginal angles at which light absorbing material is clearly visually recognizable and the values of Sound Velocity in Subject to be Examined/(Channel Pitch of Ultrasonic Transducers× Center Frequency);

DESCRIPTION OF THE PREFERRED EMBODIMENTS

Next, with reference to drawings, embodiments of the present invention will be described in detail. In examples of the present invention, an ultrasound is used as an acoustic wave. Alternatively, an acoustic wave having an audible frequency may be used by selecting an appropriate frequency for a target of examination, a measurement condition and the like.

Figure 1:
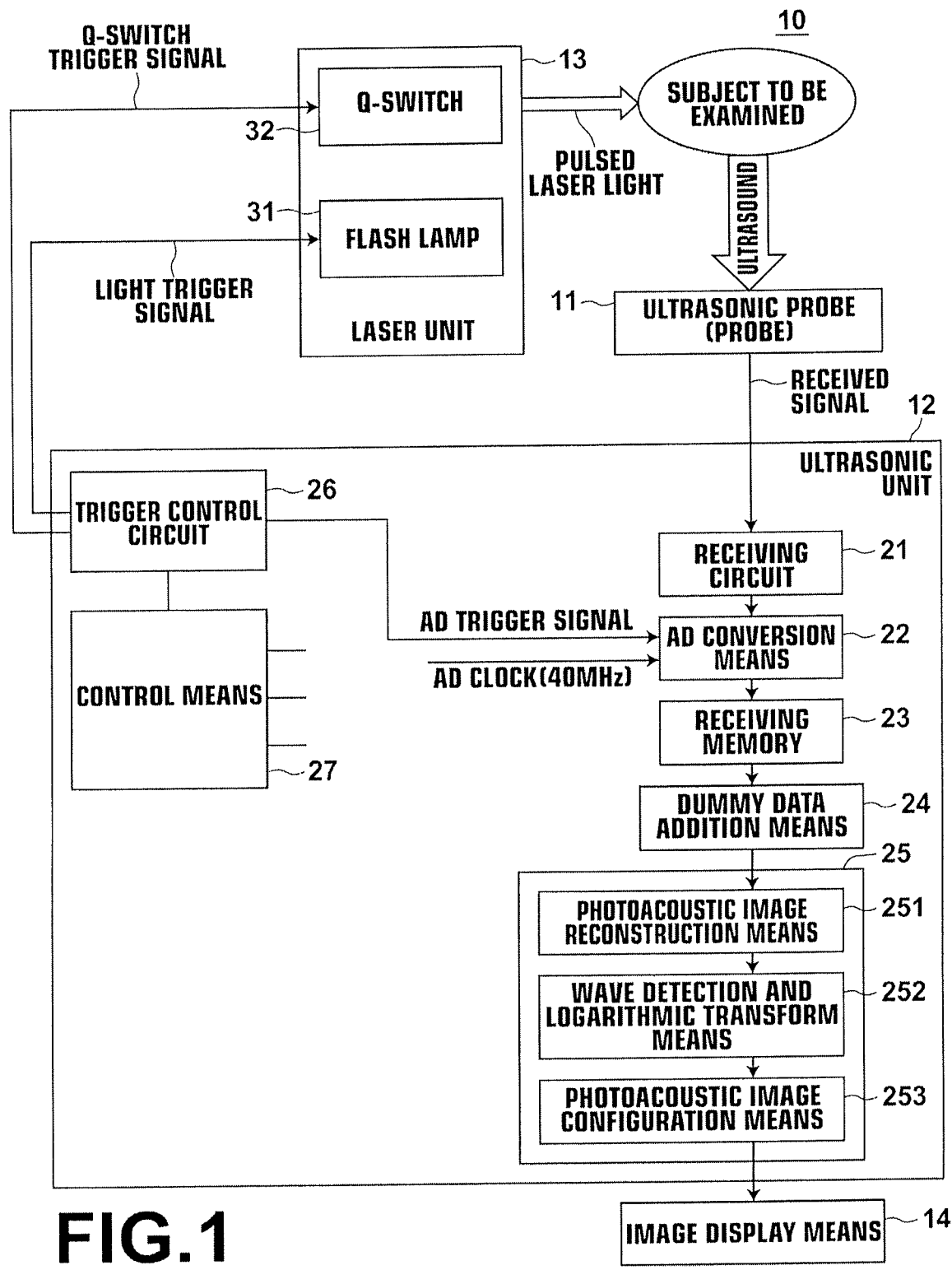
FIG. 1 is a block diagram illustrating a photoacoustic image generation apparatus according to a first embodiment of the present invention.

FIG. 1 is a diagram illustrating a photoacoustic image generation apparatus according to a first embodiment of the present invention. The photoacoustic image generation apparatus (photoacoustic image diagnosis apparatus) 10 includes a probe (ultrasonic probe) 11, an ultrasonic unit 12 and a laser unit (light source) 13. The laser unit 13 generates laser light output to a subject to be examined, such as living body tissue. The wavelength of the laser light should be appropriately set based on living body tissue or the like to be observed. The laser light output from the laser unit 13 is, for example, guided to the probe 11 by a light guide means, such as an optical fiber. Here, it is not necessary that the light output to the subject to be examined is laser light. Light other than the laser light may be output to the subject to be examined.

The probe 11 is an acoustic wave detection means, and includes plural detector elements (ultrasonic transducers) that are at least linearly arranged. The probe 11 detects, after light has been output to the subject to be examined, a photoacoustic wave induced in the subject by the output light. Further, the probe 11 includes a light output unit, and outputs, toward the subject to be examined, the light that has been guided from the laser unit 13. It is not necessary that light is output to the subject to be examined from the probe 11. The light may be output to the subject to be examined from a position other than the probe 11.

The ultrasonic unit 12 includes a receiving circuit 21, an AD conversion means 22, a receiving memory 23, a dummy data addition means 24, an image generation means 25, a trigger control circuit 26 and a control means 27. The receiving circuit 21 receives a detection signal (photoacoustic signal) of the photoacoustic wave detected by the probe 11. The AD conversion means 22 converts the photoacoustic signal received by the receiving circuit 21 to a digital signal. For example, the AD conversion means 22 performs, based on an AD clock signal of a predetermined frequency, sampling on the photoacoustic signal at a predetermined sampling cycle. The receiving memory 23 stores the photoacoustic signal on which sampling has been performed by the AD conversion means 22.

The dummy data addition means 24 reads out data of the photoacoustic wave that has been detected by each ultrasonic transducer in the probe 11 from the receiving memory 23. In the data of the photoacoustic wave (photoacoustic wave data) that have been read out, photoacoustic signals detected by the ultrasonic transducers, respectively, are arranged in accordance with the positions of the ultrasonic transducers. The dummy data addition means 24 assumes that the probe 11 includes a virtual ultrasonic transducer or transducers (virtual detector element or elements) outside of linearly-arranged plural ultrasonic transducers, and adds dummy data corresponding to the virtual ultrasonic transducer or transducers to the photoacoustic data. The value of the dummy data to be added is 0 (a signal level is 0). The image generation means 25 generates a photoacoustic image by reconstructing the photoacoustic data to which the dummy data have been added by using a Fourier transform method. The reconstruction by using the Fourier transform method includes two-dimensional Fourier transform on the photoacoustic data to which dummy data have been added, transformation (mapping) from time scale to space scale on the data on which the Fourier transform has been performed, and two-dimensional inverse Fourier transform on the data after mapping.

Figure 2:
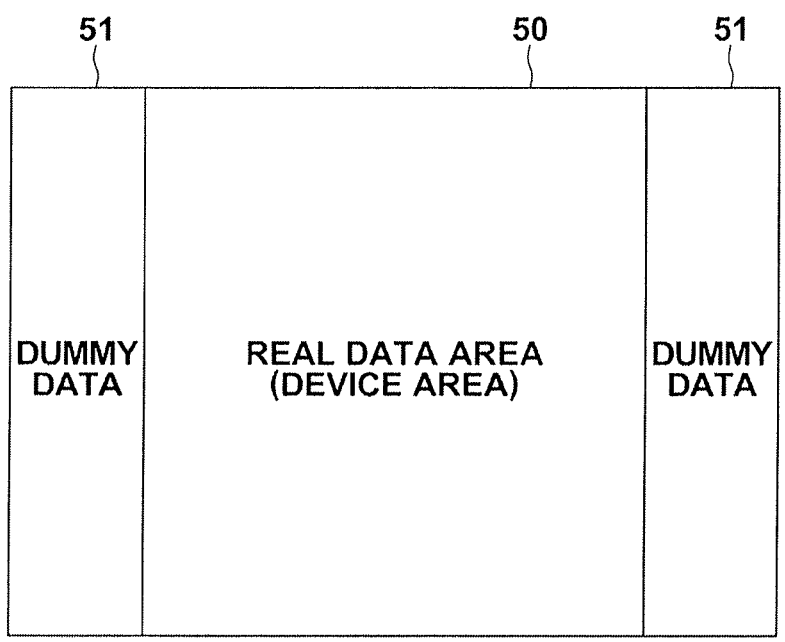
FIG. 2 is a diagram illustrating photoacoustic data to which dummy data have been added.

FIG. 2 is a diagram illustrating photoacoustic data to which dummy data have been added. A real data area 50 is an area in which signals detected by the ultrasonic transducers in the probe 11, respectively, and which have been read out from the receiving memory 23, are present. For example, when the probe 11 has 128 elements of ultrasonic transducer, the real data area 50 is an area corresponding to the 128 elements. Meanwhile, dummy data 51 are data of dummy added to an area outside of the area in which the ultrasonic transducers of the probe 11 are arranged, in other words, an area in which no corresponding ultrasonic transducer is present in the real structure of the probe 11.

For example, the dummy data addition means 24 assumes that a predetermined number of element or elements of virtual ultrasonic transducer is present on each of both sides of the linearly-arranged plural ultrasonic transducers in the direction of arrangement of the ultrasonic transducers. Further, the dummy data addition means 24 adds dummy data 51 corresponding to the predetermined number of element or elements of virtual ultrasonic transducer to each of both sides of the real data area 50. Specifically, dummy data 51 corresponding to 32 elements of virtual ultrasonic transducer are added to each of both sides of the real data area 50. Since the dummy data have been added, the photoacoustic data to which the dummy data have been added correspond to 192 elements while the number of ultrasonic transducers included in the real structure of the probe 11 is 128. Here, it is not necessary that the dummy data 51 are added to both sides of the real data area 50. The dummy data 51 may be added to one of the sides of the real data area 50.

Back to FIG. 1, the image generation means 25 includes a photoacoustic image reconstruction means 251, a wave detection and logarithmic transform means 252 and a photoacoustic image configuration means 253. The photoacoustic image reconstruction means 251 performs image reconstruction by using a Fourier transform method (FTA method) on the photoacoustic data to which the dummy data have been added. The wave detection and logarithmic transform means 252 obtains an envelope of data of each line that have been reconstructed by the photoacoustic image reconstruction means 251, and performs logarithmic transform on the obtained envelope. The photoacoustic image configuration means 253 generates a photoacoustic image based on data of each line on which logarithmic transform has been performed. For example, the photoacoustic image configuration means 253 generates the photoacoustic image by transforming the position of the photoacoustic signal (peak part) in the direction of a time axis to a position in the direction of a depth in the photoacoustic image. The image display means 14 is an image display device, such as a display device. The image display means 14 displays the generated photoacoustic image and the like.

The control means 27 controls each unit in the ultrasonic unit 12. The trigger control circuit 26 sends a flash lamp trigger signal to the laser unit 13 when the photoacoustic image is generated. Further, the trigger control circuit 26 sends a Q-switch trigger signal after outputting the flash lamp trigger signal. The laser unit 13 includes a flash lamp 31 and a Q-switch 32. When the laser unit 13 receives the flash lamp trigger signal, the laser unit 13 turns on the flash lamp 31, and starts excitation of the laser. When the Q-switch trigger signal is input to the laser unit 13, the laser unit 13 turns on the Q-switch, and outputs pulsed laser light. The trigger control circuit 26 sends a sampling trigger signal to the AD conversion means 22 synchronously with output of laser light to the subject to be examined. Accordingly, the trigger control circuit 26 controls the timing of starting sampling on the photoacoustic signal in the AD conversion means 22.

Figure 3:
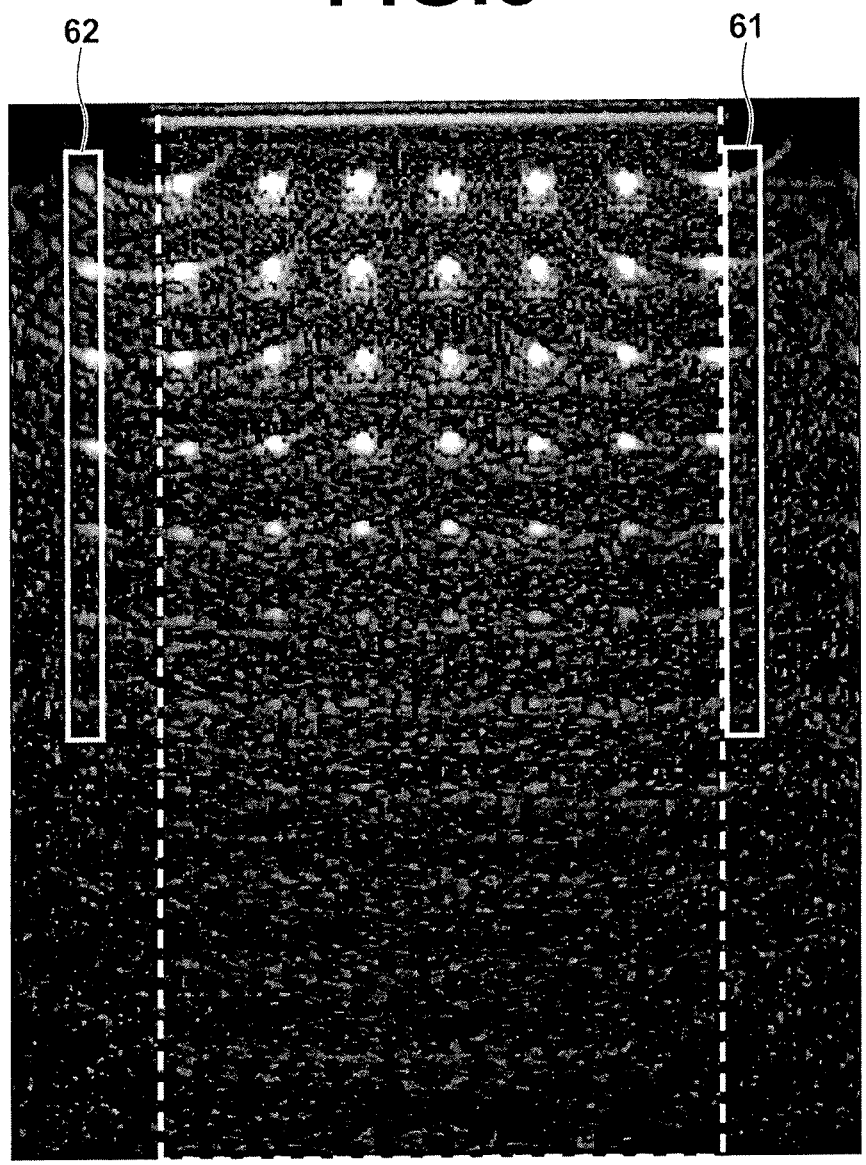
FIG. 3 is a diagram illustrating an example of a generated photoacoustic image.

FIG. 3 is a diagram illustrating an example of the generated photoacoustic image. The image illustrated in FIG. 3 is a photoacoustic image of a sample in which light absorbing material is arranged at equal intervals in the direction of arrangement of the ultrasonic transducers and in the direction of the depth of the subject to be examined. In FIG. 3, boundaries between the real data area 50 (FIG. 2) and the dummy data 51 are indicated by broken lines. A photoacoustic wave (spherical wave) from light absorbing material that is present in the real data area 50 perpendicularly enters an ultrasonic transducer of the probe 11 that is present right above the light absorbing material. Further, the photoacoustic wave obliquely enters ultrasonic transducers around the ultrasonic transducer. Therefore, it is possible to clearly recognize, in the photoacoustic image, the light absorbing material that is present in the real data area 50 by reconstructing the photoacoustic data.

Meanwhile, a photoacoustic wave from light absorbing material that is present in an area next to the real data area 50, and to which the dummy data 51 have been added, is not able to perpendicularly enter any ultrasonic transducer of the probe 11. The photoacoustic wave only obliquely enters an ultrasonic transducer or transducers at an end part or parts. In the embodiment of the present invention, the light absorbing material outside of the device area is represented in an image by using the photoacoustic wave that has obliquely entered the ultrasonic transducer or transducers at the end part or parts. Since reconstruction is performed on data including the dummy data, it is possible to generate, based on the photoacoustic wave that has entered the ultrasonic transducer or transducers at the end part or parts, an image representing the light absorbing material that is present in the area to which the dummy data 51 have been added. Consequently, it is possible to widen the field of view of the photoacoustic image (a range represented in the image).

Figure 4:
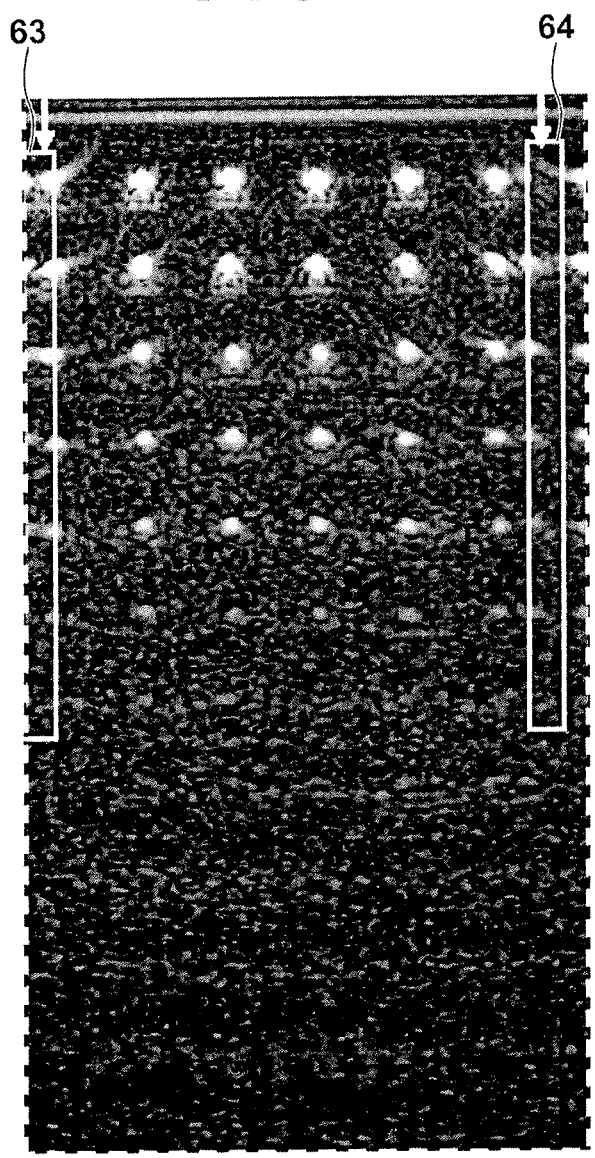
FIG. 4 is a diagram illustrating a comparative example of photoacoustic image.

FIG. 4 is a diagram illustrating a comparative example of a photoacoustic image that has been generated without adding any dummy data. The photoacoustic image illustrated in FIG. 4 is obtained by reconstructing data that are present in the real data area 50 when the photoacoustic image illustrated in FIG. 3 is obtained by using a Fourier transform method. The image size of the photoacoustic image (FIG. 3) obtained by performing reconstruction on data including the dummy data 51 is, for example, 480×600 pixels, while the image size of the photoacoustic image (FIG. 4) obtained by performing reconstruction only on the real data area 50 is, for example, 320×600 pixels.

When reconstruction of the image is performed without adding the dummy data 51, an area 61 part illustrated in FIG. 3 appears, as a wrap-around noise, in an area 64 part illustrated in FIG. 4, and that causes an artifact. Further, an area 62 part illustrated in FIG. 3 appears, as a wrap-around noise, in an area 63 part illustrated in FIG. 4, and that causes an artifact. When reconstruction by using a Fourier transform method is performed on data including the dummy data, it is possible to obtain a photoacoustic image, as illustrated in FIG. 3, in which artifacts caused by the photoacoustic wave from an area outside of the real data area 50 are suppressed.

Figure 5:
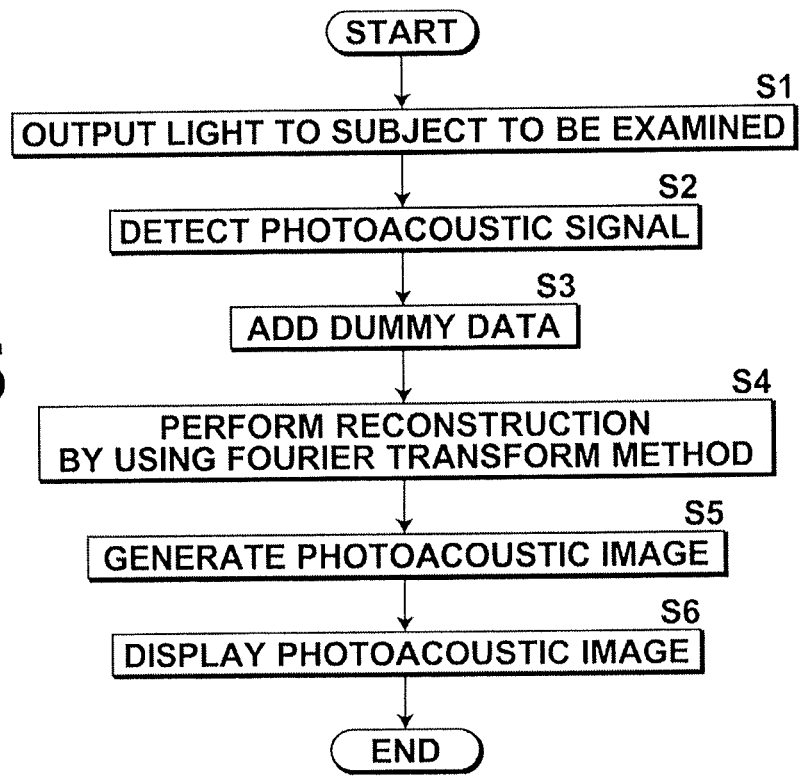
FIG. 5 is a flow chart showing operation procedures.

FIG. 5 is a diagram illustrating operation procedures. The trigger control circuit 26 outputs a flash lamp trigger signal to the laser unit 13. The laser unit 13 receives the flash lamp trigger signal, and turns on the flash lamp 31. The trigger control circuit 26 outputs a Q-switch trigger signal at predetermined timing. When the Q-switch trigger signal is input, the laser unit 13 turns on the Q-switch 32, and outputs pulsed laser light. The output pulsed laser light is, for example, guided to the probe 11, and output from the probe 11 to the subject to be examined (step S1).

The probe 11 detects, after laser light is output, a photoacoustic signal induced in the subject by the laser light output to the subject (step S2). The receiving circuit 21 in the ultrasonic unit 12 receives the photoacoustic signal detected by the probe 11. The trigger control circuit 26 sends a sampling trigger signal to the AD conversion means 22 in such a manner to be matched with the timing of outputting light to the subject to be examined. The AD conversion means 22 receives the sampling trigger signal, and starts sampling on the photoacoustic signal. The AD conversion means 22 stores sampling data of the photoacoustic signal in the receiving memory 23.

The dummy data addition means 24 reads out the sampling data of the photoacoustic signal from the receiving memory 23, and adds dummy data to the sampling data (photoacoustic data) of the photoacoustic signal, which have been read out (step S3). When the dummy data addition means 24 adds dummy data, the dummy data addition means 24 assumes, for example, that a virtual ultrasonic transducer or transducers are present on both sides of linearly arranged plural ultrasonic transducers of the probe 11 in the direction of the arrangement of the plural ultrasonic transducers. Further, the dummy data addition means 24 adds "0" (dummy data), as a detection signal of a photoacoustic wave detected by the virtual ultrasonic transducer or transducers.

The photoacoustic image reconstruction means 251 performs reconstruction by using a Fourier transform method on the photoacoustic data to which the dummy data have been added (step S4). The wave detection and logarithmic transform means 252 obtains an envelope of data of each line that have been obtained by reconstruction, and performs logarithmic transform on the obtained envelope. The photoacoustic image configuration means 253 generates a photoacoustic image based on data of each line on which logarithmic transform has been performed (step S5). The image display means 14 displays the photoacoustic image that has been generated in step S5 on a display screen (step S6).

In the embodiment of the present invention, it is assumed that the virtual ultrasonic transducer or transducers are present outside of the linearly-arranged plural ultrasonic transducers in the probe. Further, dummy data corresponding to the virtual ultrasonic transducer or transducers are added to real data of the photoacoustic wave detected by the ultrasonic transducers in the probe 11. Further, a photoacoustic image is generated from the photoacoustic data to which the dummy data have been added by using a Fourier transform method. When the photoacoustic image is generated in this manner, it is possible to reduce a wrap-around noise, which is generated when reconstruction is performed by using the Fourier transform method without adding the dummy data. Therefore, it is possible to obtain a photoacoustic image in which an artifact caused by a photoacoustic wave from a region outside of a region that corresponds to the device area is suppressed. Further, it is possible to increase the width of the photoacoustic image in a lateral direction (the direction of arrangement of ultrasonic transducers) by a width corresponding to the added dummy data. Therefore, it is possible to generate an image representing a wider range of the subject to be examined.

In detection of a photoacoustic wave, it is not necessary to use all of the ultrasonic transducers included in the probe 11. For example, a photoacoustic wave may be detected by using a part of the ultrasonic transducers included in the probe 11 to increase a frame rate, or the like. In such a case, the dummy data addition means 24 should add dummy data by assuming that a virtual ultrasonic transducer or transducers are present outside of an area in which ultrasonic transducers used in detection of the photoacoustic wave are present, in other words, an area in which data of the detected photoacoustic wave are present.

For example, when the probe 11 has 128 ultrasonic transducers that are linearly arranged, detection of a photoacoustic wave may be performed by using 64 of the ultrasonic transducers located at a center. In this case, 32 ultrasonic transducers on either side of the 64 ultrasonic transducers do not contribute to detection of the photoacoustic wave. In that case, the dummy data addition means 24 may assume that a virtual ultrasonic transducer or transducers are present at a position that at least partially overlaps with the area of the 32 ultrasonic transducers located on either side of the 64 ultrasonic transducers. Further, the dummy data addition means 24 may add the dummy data to the photoacoustic data that have been detected by the 64 photoacoustic transducers at the center. As this example shows, it is not necessary that the dummy data addition means 24 assumes that a virtual ultrasonic transducer or transducers are present at a position in which no ultrasonic transducer is present in the real structure of the probe 11.

Next, a second embodiment of the present invention will be described. The configuration of a photoacoustic image generation apparatus in the present embodiment is similar to the configuration of the photoacoustic image generation apparatus 10 in the first embodiment, which is illustrated in FIG. 1. In the description of the first embodiment, the width of an area (dummy data addition area) to which dummy data are added is a constant value. In the present embodiment, the width of the dummy data addition area is determined based on the characteristics of the subject to be examined and the probe 11. The second embodiment may be similar to the first embodiment and the like except that the width of the dummy data addition area is variable.

It is considered that a range in which light absorbing material outside of the device area is able to be represented in an image changes depending on the sensitivity (sensitivity in receiving) of the probe 11 with respect to an acoustic wave that obliquely enters the probe 11. For example, when a sensitivity of detection with respect to an acoustic wave having an angular component greater than a certain angle is low, it is considered that the probe 11 is not able to detect a photoacoustic wave from light absorbing material that is present in an area outside of a straight line extending at the angle from an ultrasonic transducer at an end. Therefore, the width of the dummy data addition area should be determined based on the characteristics of detecting the acoustic wave in an oblique direction at the probe 11. Further, the acoustic wave attenuates more while the acoustic wave travels in the subject to be examined, as the frequency is higher. Therefore, when the width of the dummy data addition area is determined, the center frequency (a frequency at which the sensitivity of detection is highest) of the detector elements should be considered.

The sensitivity in receiving in an oblique direction by the ultrasonic transducers in the probe 11 depends on Sound Velocity in Subject to be Examined/(Channel Pitch of Ultrasonic Transducers×Center Frequency). Here, the channel pitch of the ultrasonic transducers is defined by the element size of the ultrasonic transducer (the width of the ultrasonic transducer in the direction of arrangement of the ultrasonic transducers). The center frequency is defined, for example, by the thickness of a thinfilm of the ultrasonic transducer consisting of PZT (Lead Zirconate Titanate) and the thickness of an acoustic matching layer or an acoustic impedance.

Figure 6:
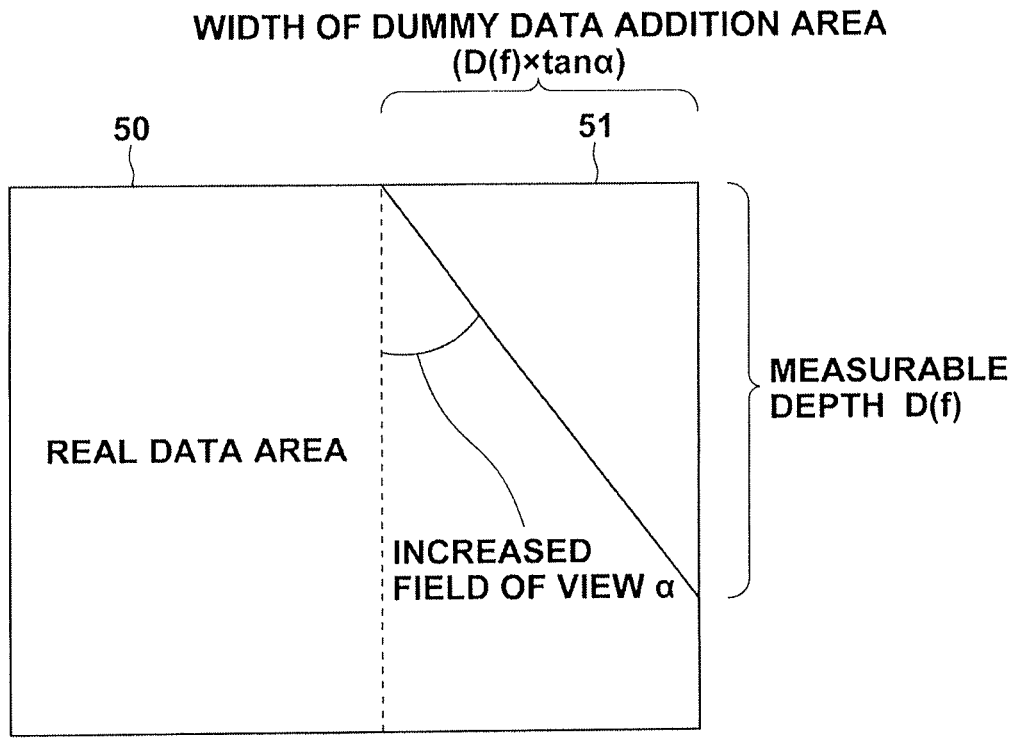
FIG. 6 is a diagram illustrating determination of the width of a dummy data addition area.

FIG. 6 is a diagram illustrating determination of the width of a dummy data addition area. The dummy data addition means 24 defines an angle with respect to a straight line perpendicular to an ultrasonic detection surface of the probe 11, as angle α of increased field of view. The dummy data addition means 24 determines, based on Sound Velocity in Subject to be Examined/(Channel Pitch of Ultrasonic Transducers×Center Frequency), increased field of view α. Further, the dummy data addition means 24 determines measurable depth (the depth of a position) D(f) based on center frequency f. The dummy data addition means 24 determines, as the width of the dummy data addition area, a length (width) greater than or equal to a value determined by D(f)×tan α. The number of element or elements of virtual ultrasonic transducer assumed by the dummy data addition means 24 may be obtained, for example, by dividing the width of the dummy data addition area by the channel pitch of the ultrasonic transducers.

FIG. 7A and FIG. 7B are diagrams illustrating photoacoustic images obtained by reconstructing data including dummy data, respectively. FIG. 7A illustrates a photoacoustic image when a photoacoustic wave has been detected by using the probe 11 of Sound Velocity in Subject to be Examined/(Channel Pitch of Ultrasonic Transducers×Center Frequency)=0.57. FIG. 7B illustrates a photoacoustic image when a photoacoustic wave has been detected by using the probe 11 of Sound Velocity in Subject to be Examined/ (Channel Pitch of Ultrasonic Transducers×Center Frequency)=1.65.

In FIG. 7A, light absorbing material is clearly visually recognizable in an area inward (toward the device area) from a straight line 71 extending, at the angle of 54° with respect to a direction perpendicular to an ultrasonic detection surface, from the position of an ultrasonic transducer at an end, as an origin, toward a dummy data addition area side. However, light absorbing material is not clearly visually recognizable in an area (toward an area opposite to the device area) outside of the straight line 71. Specifically, when the probe 11 of Sound Velocity in Subject to be Examined/(Channel Pitch of Ultrasonic Transducers×Center Frequency)=0.57 is used, a marginal angle at which light absorbing material is clearly visually recognizable in the dummy data addition area is 54°.

In FIG. 7B, light absorbing material is clearly visually recognizable in an area inward from a straight line 72 extending, at the angle of 15° with respect to a direction perpendicular to an ultrasonic detection surface, from the position of an ultrasonic transducer at an end, as an origin. However, light absorbing material is not clearly visually recognizable in an area outside of the straight line 72. Specifically, when the probe 11 of Sound Velocity in Subject to be Examined/(Channel Pitch of Ultrasonic Transducers× Center Frequency)=1.65 is used, a marginal angle at which light absorbing material is clearly visually recognizable in the dummy data addition area is 15°.

Photoacoustic images are generated by using plural probes 11 having different values of Sound Velocity in Subject to be Examined/(Channel Pitch of Ultrasonic Transducers×Center Frequency), and relationships between the values of Sound Velocity in Subject to be Examined/(Channel Pitch of Ultrasonic Transducers×Center Frequency) and marginal angles at which light absorbing material is clearly recognizable in the dummy data addition area are obtained in advance through experiments. The dummy data addition means 24 uses the relationships, and determines, based on the value of Sound Velocity in Subject to be Examined/ (Channel Pitch of Ultrasonic Transducers×Center Frequency) of the probe 11 used in detection of the photoacoustic wave, increased field of view α when the width of the dummy data addition area is determined.

FIG. 8 is a diagram illustrating a relationship between a marginal angle at which light absorbing material is clearly visually recognizable in the dummy data addition area and Sound Velocity in Subject to be Examined/(Channel Pitch of Ultrasonic Transducers×Center Frequency). In the graph illustrated in FIG. 8, plotted points represent measured values, and a straight line represents a relational expression obtained from the measured values. For example, when a probe having the value of Sound Velocity in Subject to be Examined/(Channel Pitch of Ultrasonic Transducers×Center Frequency) of 1 is used, the graph illustrated in FIG. 8 shows that the marginal angle at which light absorbing material is clearly visually recognizable in the dummy data addition area is about 35°. The dummy data addition means 24 determines that increased field of view α is 35° when the probe 11 of Sound Velocity in Subject to be Examined/ (Channel Pitch of Ultrasonic Transducers×Center Frequency) of 1 is used.

Measurable depth D(f) is obtainable as follows. For example, light is output to a sample in which light absorbing material is placed in the vicinity of a center of a device area, and a photoacoustic wave (photoacoustic signal) is detected by a probe 11 including ultrasonic transducers having certain center frequency f. A range in which a signal to noise ratio is higher than or equal to a predetermined value is studied by detecting the photoacoustic signal while the position of light absorbing material in the depth direction is changed. A maximum depth in the range in which the signal to noise ratio is higher than or equal to a predetermined ratio is determined as measurable depth D(f). The aforementioned experiment is performed by using probes having plural center frequencies f, and a relationship between the center frequency and measurable depth D(f) is obtained.

Figure 9:
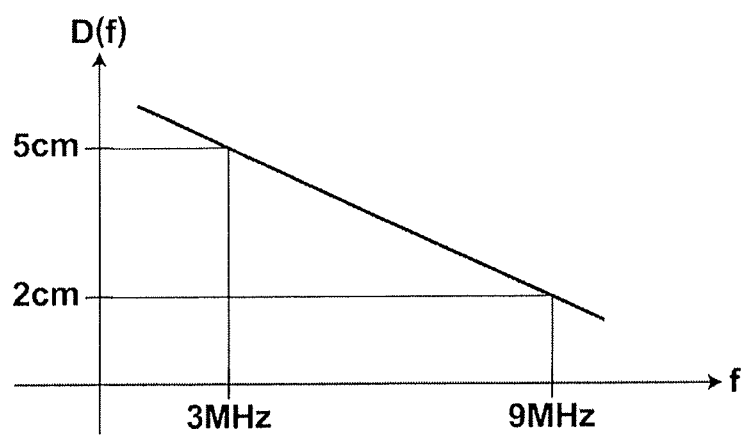
FIG. 9 is a graph showing a relationship between center frequency f and measurable depth D(f)

FIG. 9 is a diagram illustrating a relationship between center frequency f and measurable depth D(f). For example, a range of depth at which the signal to noise ratio is 2 or higher is obtained with respect to plural probes 11 having different center frequencies from each other. For example, when detection of a photoacoustic wave is performed by using a probe 11 including ultrasonic transducers having a center frequency of 3 MHz, a photoacoustic signal is detectable at a signal to noise ratio of 2 or higher in a range of 5 cm from the surface of the subject to be examined. The dummy data addition means 24 determines that measurable depth D(f) is 5 cm when the center frequency of the ultrasonic transducers is 3 MHz. Meanwhile, when detection of a photoacoustic wave is performed by using a probe 11 including ultrasonic transducers having a center frequency of 9 MHz, a photoacoustic signal is detectable at a signal to noise ratio of 2 or higher in a range of 2 cm from the surface of the subject to be examined. The dummy data addition means 24 determines that measurable depth D(f) is 2 cm when the center frequency of the ultrasonic transducers is 9 MHz. The width of the dummy data addition area is obtainable by obtaining the product of measurable depth D(f) determined in this manner and tanα (FIG. 6).

The sound velocity in the subject to be examined is a constant value when the subject to be examined is determined. Therefore, the sound velocity may be regarded as a constant, and the width of the dummy data addition area (the number of element or elements of virtual ultrasonic transducer) may be determined based the channel pitch of the ultrasonic transducers and the center frequency. More specifically, increased field of view α may be determined based on the product of the channel pitch (element size) of ultrasonic transducers and the center frequency. Further, the width of the dummy data addition area may be determined based on the increased field of view α and measurable depth D(f), which is a function of center frequency f. Alternatively, measurable depth D(f) may be a constant value (fixed value) instead of the function of center frequency f.

In the embodiment of the present invention, the width of the dummy data addition area is determined based on the characteristic of the probe 11. The width of the dummy data addition area is determined, especially, based on the sensitivity of receiving in an oblique direction of the probe 11 to be used. When the width of the dummy data addition area is a fixed width, dummy data are added, in some cases, also to an area that is not able to be represented in an image by the probe 11 used in the operation. When reconstruction is performed by adding dummy data also to the range that is not able to be represented in the image, a calculation time unnecessarily becomes long. In the embodiment of the present invention, the width of the dummy data addition area is determinable based on the characteristic of the probe 11. Therefore, it is possible to prevent addition of the dummy data even to an area in which light absorbing material is not clearly visually recognizable in a photoacoustic image after reconstruction. Hence, it is possible to avoid performing unnecessary calculations.

Figure 10:
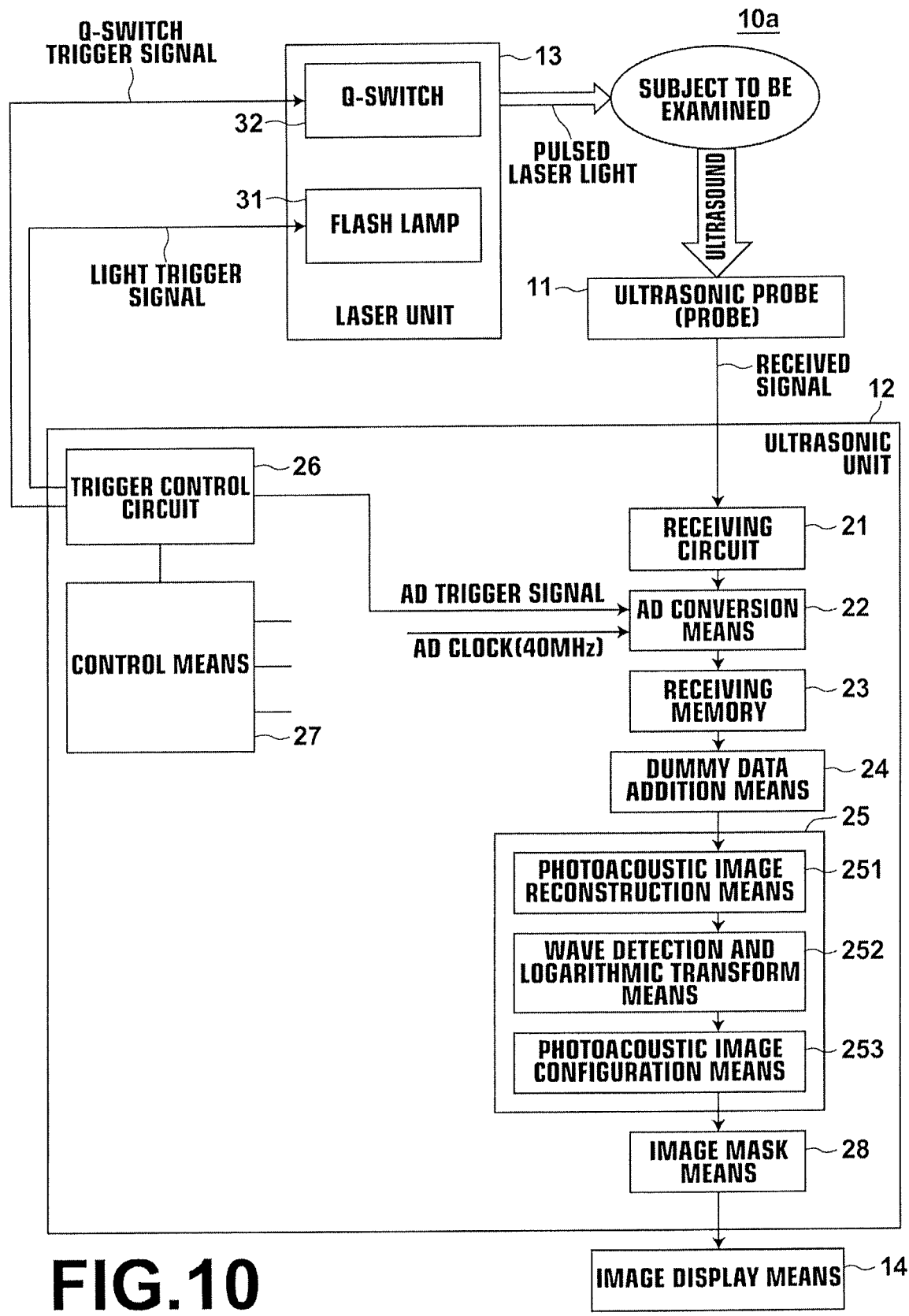
FIG. 10 is a block diagram illustrating a photoacoustic image generation apparatus in a third embodiment of the present invention.

Next, a third embodiment of the present invention will be described. FIG. 10 is a diagram illustrating a photoacoustic image generation apparatus according to the third embodiment of the present invention. A photoacoustic image generation apparatus 10*a* in the embodiment of the present invention includes an image mask means 28 in addition to the composition of the photoacoustic image generation apparatus 10 illustrated in FIG. 1. The image mask means 28 masks an area in the generated photoacoustic image outside of a straight line extending, at increased field of view α, which has been described in the second embodiment, from a pixel corresponding to an ultrasonic transducer at an end of the probe 11 toward an area in which the dummy data have been added. Other features may be similar to the second embodiment.

Figure 11:
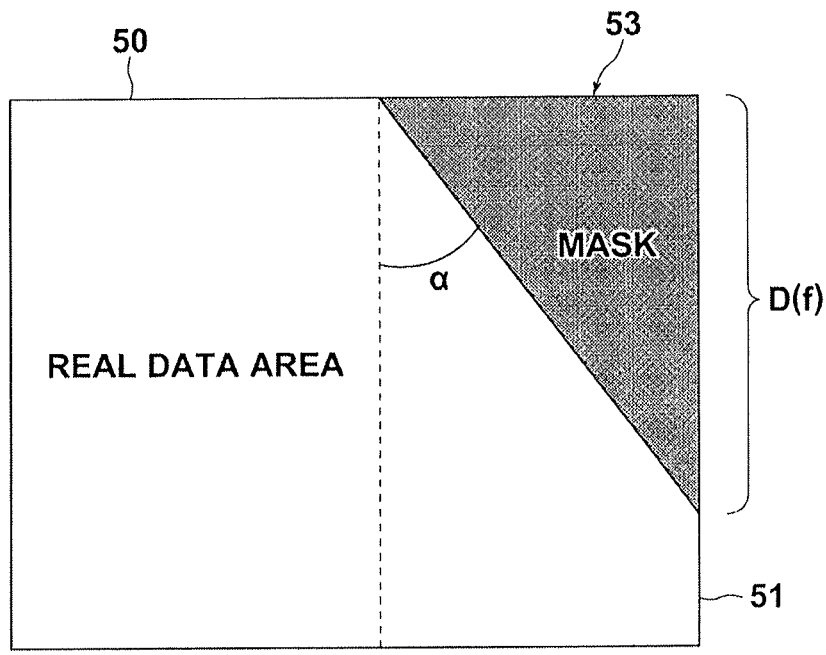
FIG. 11 is a diagram illustrating an area in which an image is masked.

FIG. 11 is a diagram illustrating an area in which an image is masked. An area corresponding to a real data area 50 of a photoacoustic image is excluded from an area to be masked. In the area in which the dummy data 51 have been added, an area in which light absorbing material is not clearly visually recognizable is determined as an area 53 to be masked. Specifically, when the width of the dummy data addition area has been determined by measurable depth D(f)×tan α, an area toward the outside (toward an area opposite to the device area) from a straight line extending, at angle α, from a pixel (a pixel at a boundary to an area to which the dummy data 51 are added) at an end of the real data area 50, as an origin, toward the dummy data addition area side is determined as the area 53 to be masked. The area 53 to be masked may be displayed, for example, by displaying in the same manner as display of a signal level of 0 (for example, black), or by displaying the same manner as display of a background (for example, white).

In the embodiment of the present invention, display of an area outside of a line at angle α in the dummy data addition area is masked. Since an area in which light absorbing material is not clearly visually recognizable is masked, it is possible to prevent an area containing only noise components from being displayed. Other effects are similar to the second embodiment.

Figure 12:
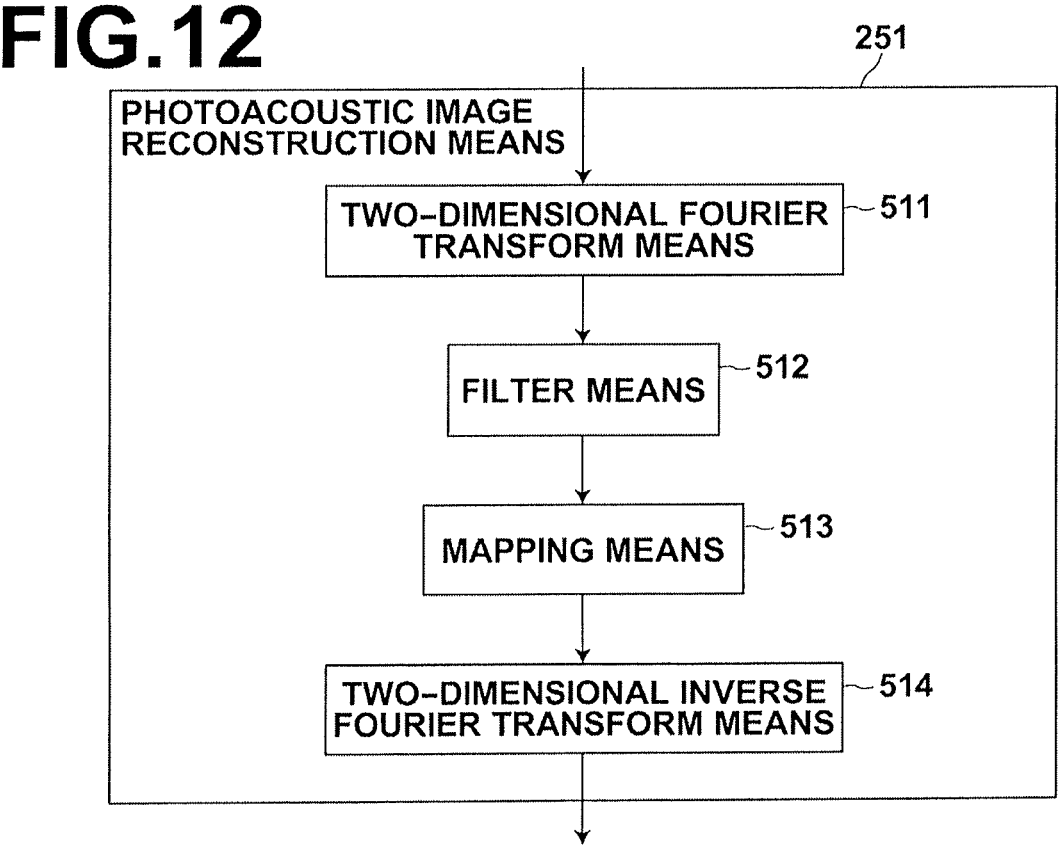
FIG. 12 is a block diagram illustrating a photoacoustic image reconstruction means in the third embodiment of the present invention.

Next, a fourth embodiment of the present invention will be described. FIG. 12 is a diagram illustrating a photoacoustic image reconstruction mans 251 in a photoacoustic image generation apparatus in the fourth embodiment of the present invention. In the embodiment of the present invention, the photoacoustic image reconstruction means 251 includes a two-dimensional Fourier transform means 511, a filter means 512, a mapping means 513 and a two-dimensional inverse Fourier transform means 514. The photoacoustic image reconstruction means 251 may be configured in a similar manner to the photoacoustic image generation apparatus in the first embodiment, illustrated in FIG. 1, or the photoacoustic image generation apparatus in the third embodiment, illustrated in FIG. 10.

The two-dimensional Fourier transform means 511 performs two-dimensional Fourier transform on the photoacoustic data to which the dummy data have been added by the dummy data addition means 24 (FIG. 1). As an algorithm of Fourier transform, for example, an algorithm of fast Fourier transform may be used. The filter means 512 is a high-cut filter. The filter means 512 cuts components higher than or equal to a predetermined frequency in the direction of arrangement of ultrasonic transducers in the probe 11 in the data on which two-dimensional Fourier transform has been performed by the two-dimensional Fourier transform means 511.

The mapping means 513 performs transformation between time scale and space scale based on the dispersion relations of sonic waves ($\omega = ck$, $\omega$: temporal frequency, and k: spatial frequency). The mapping means 513 performs transformation between time scale and space scale, for example, by performing linear interpolation mapping on photoacoustic data on which Fourier transform has been performed. The two-dimensional inverse Fourier transform means 514 performs two-dimensional inverse Fourier transform on data that have been transformed by the mapping means 513. The two-dimensional inverse Fourier transform means 514 performs inverse Fourier transform in a direction orthogonal to the direction of arrangement of ultrasonic transducers. After then, the two-dimensional inverse Fourier transform means 514 performs inverse Fourier transform in the direction of arrangement of the ultrasonic transducers.

Figure 13:
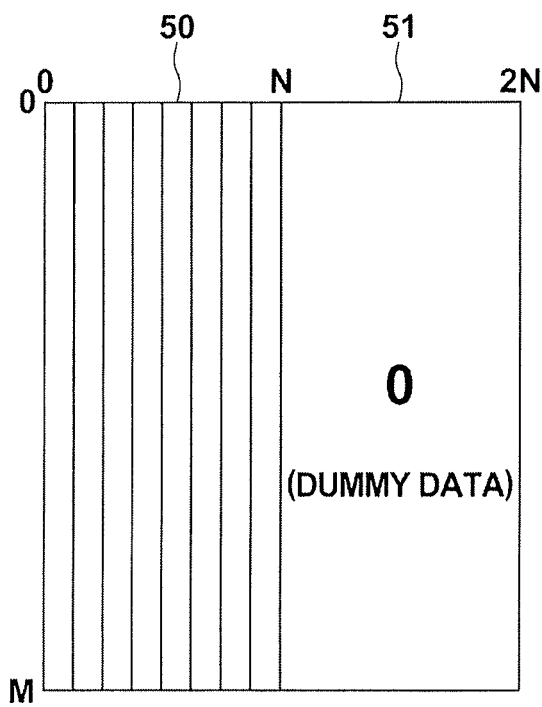
FIG. 13 is a diagram illustrating photoacoustic data to which dummy data have been added.

FIG. 13 is a diagram illustrating photoacoustic data to which the dummy data have been added. The real data area 50 is an area of photoacoustic data detected by the probe 11. Dummy data 51 are data that have been added by the dummy data addition means 24. For example, the first column through the N-th column correspond to the real data area 50, and the (N+1)th column through the 2N-th column correspond to the dummy data 51. The number of data points in each column is assumed to be M. The two-dimensional Fourier transform means 511 performs two-dimensional Fourier transform, for example, on photoacoustic data of 2N columns×M rows, to which dummy data have been added, as illustrated in FIG. 13.

Figure 14:
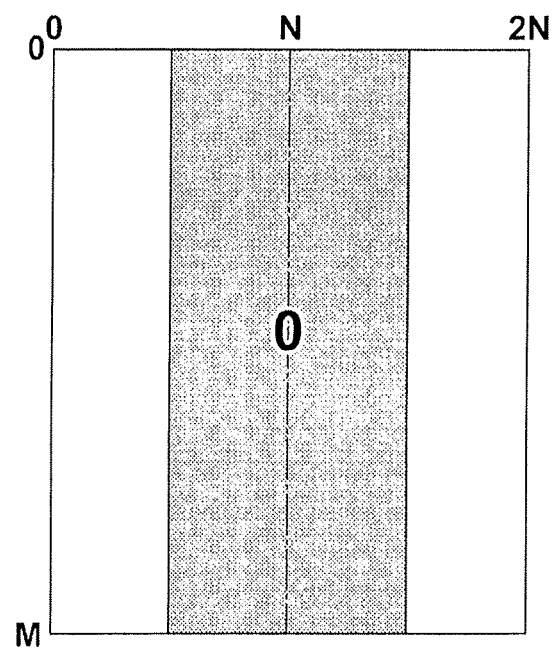
FIG. 14 is a diagram illustrating photoacoustic data in which high frequency components have been cut.

FIG. 14 is a diagram illustrating photoacoustic data in which high frequency components have been cut by the filter means 512. The filter means 512 cuts high frequency components by replacing high frequency components in the direction of arrangement of the ultrasonic transducers of the data on which two-dimensional Fourier transform has been performed with 0. A cutoff position may be, for example, N/4 through N/2. For example, when the cutoff position is N/2, the filter means 512 replaces data in the range of N/2-th column through 3N/2-th column with 0. The mapping means 513 performs mapping by linear interpolation for each column on data in which high frequency components have been cut, as illustrated in FIG. 14. At this time, interpolation processing is not needed as for a column or columns of data set to "0". Therefore, it is possible to increase the speed of operation processing.

Figure 15:
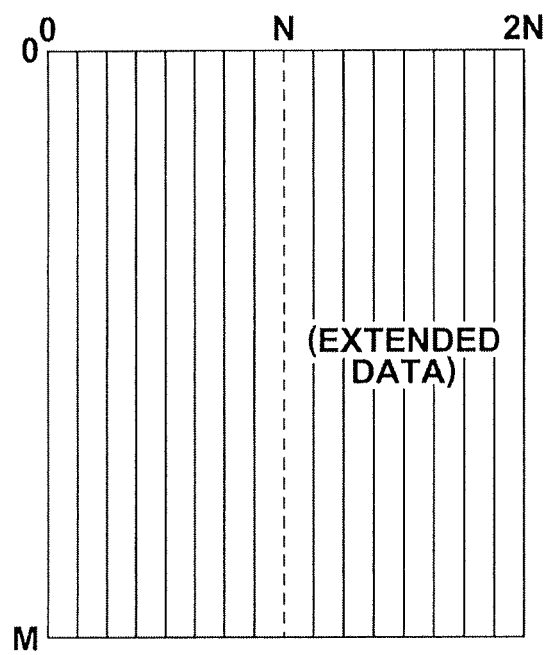
FIG. 15 is a diagram illustrating a reconstruction image in which two-dimensional inverse Fourier transform has been performed.

FIG. 15 is a diagram illustrating a reconstructed image on which two-dimensional inverse Fourier transform has been performed. The two-dimensional inverse Fourier transform means 514 generates a reconstructed image by performing two-dimensional inverse Fourier transform on data on which matching has been performed by the matching means 513. In two-dimensional inverse Fourier transform, first, Fourier inverse transform is performed for each column. At this time, processing is not needed as for a column or columns of data set to "0". Therefore, it is possible to increase the speed of operation processing. The two-dimensional inverse Fourier transform means 514 performs inverse Fourier transform on each row after performing inverse Fourier transform on each column. The size of the reconstructed image in the direction of arrangement of the ultrasonic transducers is extended by a size corresponding to the added dummy data. When an image is displayed, the range of 3N/2 through 2N should be arranged toward the left side of the 0-th column facing the paper.

Figure 16:
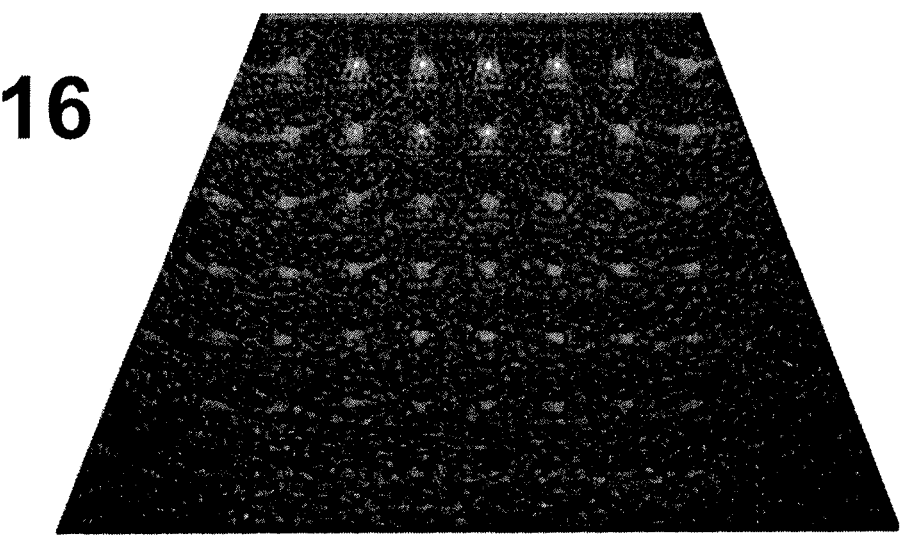
FIG. 16 is a diagram illustrating a photoacoustic image when high frequency components have been cut in reconstruction.
Figure 17:
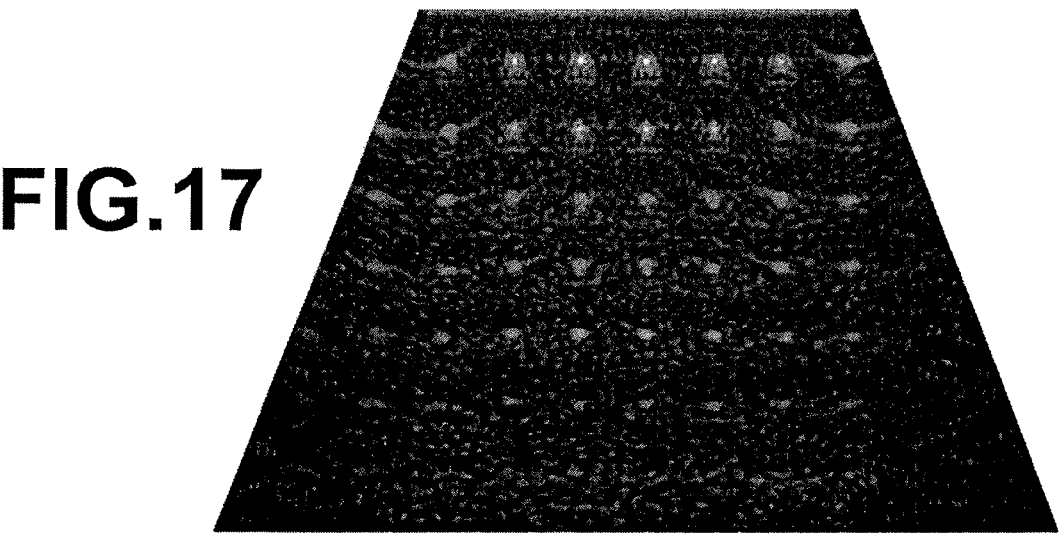
FIG. 17 is a diagram illustrating a photoacoustic image when the high frequency components are not cut.
Figure 18:
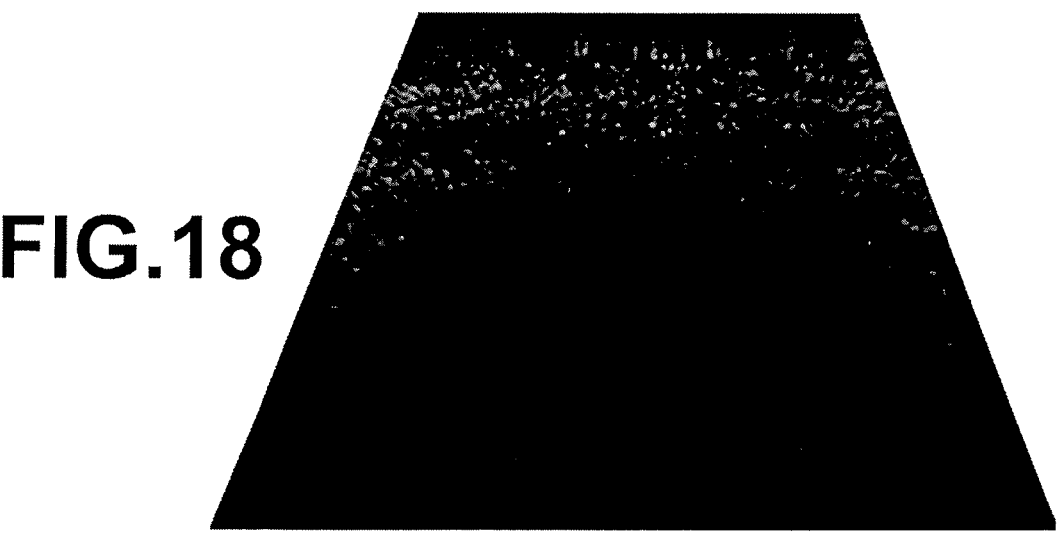
FIG. 18 is a diagram illustrating a differential image between the photoacoustic image illustrated in FIG. 16 and the photoacoustic image illustrated in FIG. 17.

FIG. 16 is a diagram illustrating a photoacoustic image when high frequency components have been cut in reconstruction. Here, a cutoff position is assumed to be N/4. FIG. 17 is a diagram illustrating a photoacoustic image when high frequency components are not cut. FIG. 18 is a diagram illustrating a differential image between the photoacoustic image illustrated in FIG. 16 and the photoacoustic image illustrated in FIG. 17. Since the high frequency components were cut, it was possible to reduce the noise components by a component corresponding to the differential image illustrated in FIG. 18.

In the embodiment of the present invention, high frequency components in the direction of arrangement of ultrasonic transducers in the data on which two-dimensional Fourier transform has been performed are cut in reconstruction by using a Fourier transform method. Since the high frequency components are cut, it is possible to reduce the noise component. Further, since the high frequency components are cut, and linear interpolation mapping is performed after data of a column or columns corresponding to the high frequency components are replaced with 0, it is possible to reduce a target of processing when mapping is performed. Hence, it is possible to increase the speed of processing. Further, in two-dimensional inverse Fourier transform, when inverse Fourier transform on each column is performed first, processing on a column or columns in which data have been replaced with 0 is not needed. Therefore, it is possible to increase the speed of processing.

In the descriptions of each of the aforementioned embodiments, the photoacoustic image reconstruction means 251 was assumed to perform two-dimensional Fourier transform on photoacoustic data corresponding to a cross section. However, it is not necessary that processing is performed in such a manner. Alternatively, an image may be reconstructed by performing three-dimensional Fourier transform on photoacoustic volume data. Further, the probe 11 in which plural ultrasonic transducers are two-dimensionally arranged may be used.

The number of virtual ultrasonic transducers (the width of dummy data addition area) that are assumed to be present by the dummy data addition means 24 may be determined, in advance, for each probe to be used. For example, the dummy data addition means 24 stores the kind of a probe 11 (ID: identifier) and the number of virtual ultrasonic transducers when the probe 11 with the ID is used in such a manner to be correlated to each other. After the probe 11 is connected to the ultrasonic unit 12, the dummy data addition means 24 obtains an ID of the probe 11 from the probe 11. The dummy data addition means 24 may add dummy data by assuming that the same number of virtual ultrasonic transducer or transducers as the number stored in such a manner to be correlated to the ID obtained from the probe 11 are present.

In the third embodiment, a case in which display outside of angle α is masked when the width of the dummy data addition area is variable has been described. However, it is not necessary that the display is masked in such a manner. Alternatively, in the first embodiment in which the width of the dummy data addition area is constant, increased field of view α may be obtained based on the value of Sound Velocity in Subject to be Examined/(Channel Pitch of Ultrasonic Transducers×Center Frequency). Further, display outside of the obtained angle α may be masked.

So far, the present invention has been described based on preferable embodiments. However, the photoacoustic image generation apparatus and method of the present invention is not limited to the aforementioned embodiments. Various modifications and changes are possible without departing from the scope of the present invention.

What is claimed is:

1. A photoacoustic image generation apparatus comprising:

an acoustic wave detector that includes a plurality of detector elements arranged in a line, and detects, after light has been output to a subject to be examined, photoacoustic wave induced in the subject by the output light to produce photoacoustic signal;

an AD convertor that samples the photoacoustic signal to produce photoacoustic data;

a dummy data adder that adds dummy data that corresponds to at least one virtual detector element to the photoacoustic data, the at least one virtual detector element being arranged outside the plurality of the detector elements in a direction of arrangement of the detector elements along with the line of the detector elements by a channel pitch that is the same as a channel pitch of the detector elements, such that pieces of the photoacoustic data and pieces of the dummy data are arranged in accordance with the positions of the detector elements and the positions of the at least one of the virtual detector element respectively, and the photoacoustic data to which the dummy data have been added is two-dimensional data, wherein the dummy data is added to each of both sides of a real data area; and an image generator that generates a two-dimensional photoacoustic image by reconstructing the photoacoustic data to which the dummy data have been added by using a two-dimensional Fourier transform method, the image generator generates a two dimensional photoacoustic image in which a dummy data area corresponding to the at least one virtual detector element is formed outside of an actual data area corresponding to the plurality of detector elements, and wherein the reconstruction by using the Fourier transform method includes performing two-dimensional Fourier transform on the photoacoustic data to which the dummy data have been added and performing two-dimensional inverse Fourier transform on the photoacoustic data on which the two-dimensional Fourier transform has been performed.

2. The photoacoustic image generation apparatus, as defined in claim 1, wherein the reconstruction by using the Fourier transform method includes:

performing two-dimensional Fourier transform on the photoacoustic data to which the dummy data have been added, cutting components higher than or equal to a predetermined frequency in a direction of arrangement of the detector elements in the photoacoustic data on which the two-dimensional Fourier transform has been performed, and performing two-dimensional inverse Fourier transform on the photoacoustic data on which the components has been cut.

3. The photoacoustic image generation apparatus, as defined in claim 1, wherein the two-dimensional inverse Fourier transform is performed by performing one-dimensional inverse Fourier transform in the direction of arrangement of the detector elements after performing one-dimensional inverse Fourier transform in a direction orthogonal to the direction of arrangement of the detector elements.

4. The photoacoustic image generation apparatus, as defined in claim 1, wherein the dummy data are 0.

5. The photoacoustic image generation apparatus, as defined in claim 1, wherein the dummy data adder assumes that the at least one virtual detector element is present on both sides of a linearly arranged plurality of detector elements in the direction of arrangement of the detector elements.

6. The photoacoustic image generation apparatus, as defined in claim 1, wherein the dummy data adder assumes that the at least one virtual detector element is present on one side of a linearly arranged plurality of detector elements in the direction of arrangement of the detector elements.

7. The photoacoustic image generation apparatus, as defined in claim 1, where an angle from a straight line perpendicular to an acoustic wave detection surface of the acoustic wave detector is $\alpha$ and the center frequency is f, and a depth determined based on the center frequency f is D(f), the angle $\alpha$ is determined based on a value obtained by dividing the sound velocity of an acoustic wave traveling in the subject to be examined by the product of the channel pitch of the detector elements and the center frequency of the detector elements, the number of the at least one virtual detector element is determined such that the at least one virtual detector elements is arranged at the channel pitch within a length represented by a product of D(f) and tan $\alpha$.

8. The photoacoustic image generation apparatus, as defined in claim 7, wherein the depth D(f) represents a maximum depth which is determined by detecting a photoacoustic signal in plural positions in a depth direction of a sample subject with the detector elements having the center frequency f and specifying at least one of signal to noise ratio higher than a predetermined value from the detected the photoacoustic signals and obtaining at least one of depth corresponding to the at least one of signal and determining the maximum depth of the obtained at least one of depth.

9. The photoacoustic image generation apparatus, as defined in claim 7, wherein the number of the at least one virtual detector element is determined based on a value obtained by dividing the length represented by the product of D(f) and tan $\alpha$ by a channel pitch of the detector elements in the acoustic wave detector.

10. The photoacoustic image generation apparatus, as defined in claim 7, the apparatus further comprising:

an image masker that masks, a mask area in the generated two-dimensional photoacoustic image, wherein the mask area is an area from a mask line, which includes a pixel corresponding the detector element of the end of the detector elements arranged in the line, toward opposite to an area including pixels corresponding the detector elements arranged in the line, the mask line is a straight line extending at the angle $\alpha$ from a straight line in the two-dimensional photoacoustic image corresponding to a straight line perpendicular to an acoustic wave detection surface of the acoustic wave detector and extending outside an real data area in the two-dimensional photoacoustic image, wherein the real data area is an area generated from the photoacoustic data obtained by the detector elements.

11. The photoacoustic image generation apparatus, as defined in claim 1, wherein the number of the at least one virtual detector element is determined in advance for each acoustic detector to be used.

12. A photoacoustic image generation method comprising the steps of:

detecting, after light has been output to a subject to be examined, a photoacoustic wave induced in the subject by the output light to produce photoacoustic signal by using an acoustic wave detector including a plurality of detector elements arranged in a line;

sampling the photoacoustic signal to produce photoacoustic data by an AD convertor;

adding dummy data corresponding to the at least one virtual detector element to the photoacoustic data, the at least one virtual detector element being arranged outside the plurality of the detector elements in a direction of arrangement of the detector elements along with the line of the detector elements by a channel pitch that is the same as a channel pitch of the detector elements, such that pieces of the photoacoustic data and pieces of the dummy data are arranged in accordance with the positions of the detector elements and the positions of the at least one of the virtual detector element respectively, and the photoacoustic data to which the dummy data have been added is two-dimensional data, wherein the dummy data is added to each of both sides of a real data area; and generating a two-dimensional photoacoustic image by reconstructing the photoacoustic data to which the dummy data have been added by using a two-dimensional Fourier transform method, wherein a dummy data area corresponding to the at least one virtual detector element is formed in the two dimensional photoacoustic image outside of an actual data area which is an area corresponding to the detector elements and wherein the reconstruction by using the Fourier transform method includes performing two-dimensional Fourier transform on the photoacoustic data to which the dummy data have been added and performing two-dimensional inverse Fourier transform on the photoacoustic data on which the two-dimensional Fourier transform has been performed.

13. The photoacoustic image generation method, as defined in claim 12, wherein the reconstruction by using the Fourier transform method includes:
   performing two-dimensional Fourier transform on the photoacoustic data to which the dummy data have been added,
   cutting components higher than or equal to a predetermined frequency in a direction of arrangement of the detector elements in the photoacoustic data on which the two-dimensional Fourier transform has been performed, and
   performing two-dimensional inverse Fourier transform on the photoacoustic data on which the components has been cut.

14. The photoacoustic image generation method, as defined in claim 12, wherein the two-dimensional inverse Fourier transform is performed by performing one-dimensional inverse Fourier transform in the direction of arrangement of the detector elements after performing one-dimensional inverse Fourier transform in a direction orthogonal to the direction of arrangement of the detector elements.

15. The photoacoustic image generation method, as defined in claim 12, wherein the dummy data are 0.

16. The photoacoustic image generation method, as defined in claim 12, wherein in the step of adding the dummy data, it is assumed that the at least one virtual detector element is present on both sides of a linearly arranged plurality of detector elements in the direction of arrangement of the detector elements.

17. The photoacoustic image generation method, as defined in claim 12, wherein in the step of adding the dummy data, it is assumed that the at least one virtual detector element is present on one side of a linearly arranged plurality of detector elements in the direction of arrangement of the detector elements.

18. The photoacoustic image generation method, as defined in claim 12, where an angle from a straight line perpendicular to an acoustic wave detection surface of the acoustic wave detector is $\alpha$ and the center frequency is f, and a depth determined based on the center frequency f is D(f), the angle a is determined based on a value obtained by dividing the sound velocity of an acoustic wave traveling in the subject to be examined by the product of the channel pitch of the detector elements and the center frequency of the detector elements, the number of the at least one virtual detector element is determined such that the at least one virtual detector elements is arranged at the channel pitch within a length represented by a product of D(f) and tan $\alpha$.

19. The photoacoustic image generation method, as defined in claim 18, wherein the depth D(f) represents a maximum depth which is determined by detecting a photoacoustic signal in plural positions in a depth direction of a sample subject with the detector elements having the center frequency f and specifying at least one of signal to noise ratio higher than a predetermined value from the detected the photoacoustic signals and obtaining at least one of depth corresponding to the at least one of signal and determining the maximum depth of the obtained at least one of depth.

20. The photoacoustic image generation method, as defined in claim 18, wherein the number of the at least one virtual detector element is determined based on a value obtained by dividing the length represented by the product of D(f) and tan $\alpha$ by a channel pitch of the detector elements in the acoustic wave detector.

21. The photoacoustic image generation method, as defined in claim 13, the method further comprising:
   the step of masking, a mask area in the generated two-dimensional photoacoustic image, wherein the mask area is an area from a mask line, which includes a pixel corresponding the detector element of the end of the detector elements arranged in the line, toward opposite to an area including pixels corresponding the detector elements arranged in the line, the mask line is a straight line extending at the angle a from a straight line in the two-dimensional photoacoustic image corresponding to a straight line perpendicular to an acoustic wave detection surface of the acoustic wave detector and extending outside an real data area in the two-dimensional photoacoustic image, wherein the real data area is an area generated from the two-dimensional photoacoustic data obtained by the detector elements.

22. The photoacoustic image generation method, as defined in claim 12, the method further comprising the step of determining the number of the at least one virtual detector element in advance for each acoustic detector to be used.

* * * * *